(12) United States Patent
Soglowek et al.

(10) Patent No.: US 6,852,775 B1
(45) Date of Patent: Feb. 8, 2005

(54) POLYMERIZABLE DENTAL COMPOSITIONS

(75) Inventors: Wolfgang Soglowek, Diessen-Obermühlhausen (DE); Keith O'Connell, Maidenhead (GB)

(73) Assignee: 3M ESPE AG, Seefeld (DE)

( * ) Notice: Subject to any disclaimer, the term of this patent is extended or adjusted under 35 U.S.C. 154(b) by 231 days.

(21) Appl. No.: 10/018,660

(22) PCT Filed: Jun. 21, 2000

(86) PCT No.: PCT/EP00/05737

§ 371 (c)(1), (2), (4) Date: Mar. 6, 2002

(87) PCT Pub. No.: WO00/78271

PCT Pub. Date: Dec. 28, 2000

(30) Foreign Application Priority Data

Jun. 21, 1999 (DE) .......................... 199 28 238

(51) Int. Cl.[7] .......................... A61K 6/10; A61K 6/083; C08F 2/44; C08F 4/40

(52) U.S. Cl. ...................... 523/109; 523/113; 523/115; 523/120; 526/217; 526/220; 526/227

(58) Field of Search .................. 526/217, 220, 526/227; 523/109, 113, 115, 120

(56) References Cited

U.S. PATENT DOCUMENTS

| | | |
|---|---|---|
| 4,443,587 A | 4/1984 | Schmitt et al. |
| 4,544,742 A | 10/1985 | Schmitt et al. |
| 4,866,146 A | 9/1989 | Janda et al. |
| 5,583,164 A | 12/1996 | Jochum et al. |
| 5,688,883 A | 11/1997 | Klee et al. |
| 5,968,998 A | 10/1999 | Jochum et al. |
| 6,147,136 A | 11/2000 | Bissinger |

FOREIGN PATENT DOCUMENTS

| | | |
|---|---|---|
| DE | 37 30921 A1 | 3/1989 |
| DE | 197 42 980 A1 | 4/1999 |
| EP | 0 059 451 A1 | 8/1982 |
| EP | 0 374 824 A2 | 6/1990 |
| EP | 0 508 095 B1 | 10/1992 |
| EP | 0 732 098 A2 | 9/1996 |
| GB | 2 094 326 * | 9/1982 |
| IE | 920833 | 9/1992 |
| JP | 2245080 | 9/1990 |
| WO | WO 96 19179 A | 6/1996 |

* cited by examiner

Primary Examiner—Tae H. Yoon
(74) Attorney, Agent, or Firm—Birch, Stewart, Kolasch & Birch, LLP

(57) ABSTRACT

The invention relates to polymerizable dental compositions which contain (a) 10 to 98.999 wt.-% of at least one bi- or higher-functional ethylenically unsaturated monomer, (b) 0 to 88.999 wt.-% of at least one monofunctional ethylenically unsaturated monomer, (c) 0 to 5 wt.-% of an accelerator, (d) 0.001 to 5 wt.-% of a redox initiator system which can trigger the radical polymerisation and (e) 0 to 88.999 wt.-% fillers, thixotropic auxiliaries, retarders and other auxiliaries (f) 1 to 30 wt.-% of a customary plasticizer and are characterized in that the redox initiator system comprises (i) a barbituric acid derivative and/or a malonyl sulfamide and (ii) an organic peroxide, selected from the group of the mono- or multifunctional carboxylic acid peroxyesters, and the constituents (a) to (f) are present in two pastes spatially separated from each other. The dental compositions are suitable as filling material, stump build-up material, fixing cement, temporary crown and bridge material, dental material or for the preparation of inlays, onlays, facing shells, modelling materials.

43 Claims, No Drawings

POLYMERIZABLE DENTAL COMPOSITIONS

This application is the national phase under 35 U.S.C. § 371 of PCT International Application No. PCT/EP00/05737 which has an International filing date of Jun. 21, 2000, which designated the United States of America and was published in English.

The present invention relates to polymerisable dental compositions which contain
- a) 10 to 98.999 wt.-% of at least one bi- or higher-functional ethylenically unsaturated monomer,
- b) 0 to 88.999 wt.-% of at least one monofunctional ethylenically unsaturated monomer,
- c) 0 to 5 wt.-% of an accelerator,
- d) 0.001 to 5 wt.-% of a redox initiator system which can trigger the radical polymerisation,
- e) 0 to 88.999 wt.-% fillers, thixotropic auxiliaries, retarders and other auxiliaries and
- f) 1 to 30 wt.-% of a customary plasticizer.

Polymerisable dental compositions are suitable in particular as filling materials, stump build-up materials, fixing cements, temporary crown and bridge materials, dental materials, modelling materials or for the preparation of inlays, onlays, facing shells and temporary crowns and bridges.

Depending on the intended use, thinly liquid to viscoplastic compositions are involved which can be provided with organic or inorganic fillers, and cure during polymerisation.

Above all, ethylenically unsaturated compounds, such as acrylic acid and/or methylacrylic acid esters, are used as monomers of the polymerisable dental compositions.

The temporary crown and bridge materials are normally relatively low-filled systems which contain approx. 10 to 70 wt.-% inorganic filler. The fillers used have an average particle size of 1 to 15 μm. In addition however, much finer fillers in the range from 0.02 to 0.05 μm are also used with the above named fillers, in order to make the materials sufficiently plastic and thixotropic. The use of organic fillers, such as e.g. polymethyl methacrylate, has also proved successful. acceptable in the dental field. In addition, tertiary aromatic amines can be used only under certain conditions due to their health risk. Furthermore, the increase in temperature during polymerisation of these systems, due to the exothermic reaction processes, causes problems. Too great a development of heat can lead to damage to the patient's pulpa.

The initiator systems which are described in the German patent specification DE-C-14 95 520 have a more favourable temperature development and also better colour stability. The composition from DE-C-14 95 520 polymerises at low temperature in a short time and without using external energy. The systems described contain barbituric acid derivatives or malonyl sulfamides, organic peroxides, ionogenically bound halogen and/or a heavy metal compound. European patent specification EP-B-0 374 824 describes such an initiator system comprising barbituric acid derivative, peroxide, heavy metal compound and ionogenic halogen. Barbituric acid derivatives or malonyl sulfamides and peroxides cannot be stored together in these initiator systems. Furthermore, both named constituents of the initiator systems also have to be stored separately from the monomers. A storage in three pastes spatially separated from each other is necessary to provide polymerisable dental compositions which contain monomers, barbituric acid derivatives or malonyl sulfamides, organic peroxides, ionogenically bound halogen and/or a heavy metal compound.

This leads to a relatively costly handling of the systems. Three-component systems are not suitable for an automatic mixing. Therefore these conventional dental compositions comprising three components have to be mixed by hand, air being introduced and the dispensing of the individual components not being able to be so precise. The introduction of air is to be avoided above all because defects occur in the cured material, caused by introduced air bubbles. The fracture sensitivity increases and a poor surface condition results. Different dosages lead to changed setting times, poorer mechanical properties and an imprecise colouration. Furthermore, mixing by hand is more time-consuming than automatic mixing.

Alternatively, there is the possibility, as described e.g. in JP-A-02245080, to make barbituric acid derivatives and organic peroxides in the form of a powder available. Such powder-liquid systems are also described in DE-A-197 42 980 and U.S. Pat. No. 5,688,883. The peroxide component is contained in a solution, while the powder component has a barbituric acid derivative.

A two-component system with the named constituents is described in the German patent specification DE-C-37 25 502. This, however, is a powder-liquid system in which barbituric acid derivatives or malonyl sulfamides and peroxides are present as powder and there is adequate storage stability, because the two components do not react with each other to a noteworthy extent when in powdery state. The awkward handling is a disadvantage with such a powder-liquid system. For example, because of the powder proportion, these systems cannot be used in mixing devices customary in the trade in dentistry, which are designed for paste-paste systems. In addition, more time is required for the mixing of a polymerisable dental composition comprising powder and liquid than for the mixing of pastes and there is the danger that air is introduced, with the above described disadvantages.

Two-component, automatically mixable paste-paste systems comprising the constituents which are listed in the named printed documents DE-C-37 25 502, DE-C-14 95 520 and EP-B-0 375 824, were hitherto unable to be prepared with sufficient storage stability.

It is thus the object of the present invention to make available a polymerisable dental composition, the initiator system of which contains (i) barbituric acid derivatives and/or malonyl sulfamides and (ii) organic peroxides as well as optionally ionogenic halogens and heavy metal compounds, the constituents of which can be present in two components in the form of pastes spatially separated from each other, and which have a sufficient storage stability. As a rule, such compositions should be able to be stored for at least one year, in order to still have reasonable residual lives and use-by dates after being sold to the dentist.

This object is achieved by the provision of a dental composition which contains
- a) 10 to 98.999 wt.-% of at least one bi- or higher-functional ethylenically unsaturated monomer,
- b) 0 to 88.999 wt.-% of at least one monofunctional ethylenically unsaturated monomer,
- c) 0 to 5 wt.-% of an accelerator
- d) 0.001 to 5 wt.-% of a redox initiator system which can trigger the radical polymerisation,
- e) 0 to 88.999 wt.-% fillers, thixotropic auxiliaries, retarders and other auxiliaries and
- f) 1 to 30 wt.-% of a customary plasticizer and is characterized in that the redox initiator system comprises (i) a barbituric acid derivative and/or a malonyl sulfamide and (ii) an organic peroxide, selected from the group of the mono- or multifunctional carboxylic acid peroxyesters, and the constituents (a) to (f) are present in two pastes spatially separated from each other.

Surprisingly, it was found that, because of the special use of an organic peroxide from the group of the mono- or multifunctional carboxylic acid peroxyesters, the constituents of the polymerisable dental composition (a) to (f) can be present in two pastes spatially separated from each other. In the case of the preparations known from the state of the art, such an administration was not possible since, as already described above, in that component which at the same time contained (i) a barbituric acid derivative and/or a malonyl sulfamide and (ii) a customary organic peroxide, these two components reacted with each other within a short storage period and, as a result, a setting no longer occurred within a reasonable period of time after the addition of the monomer-containing component.

When using the organic peroxides according to the invention, it has been found, contrary to expectation, that a component which at the same time contains (i) a barbituric acid derivative and/or a malonyl sulfamide and (ii) an organic peroxide has an adequate storage stability, so that a provision in the form of two pastes spatially separated from each other becomes possible.

The two pastes spatially separated from each other can be prepared as base and catalyst pastes, the base paste containing the constituents (a), (b) and (c) and the catalyst paste the constituents (d) and (f). Furthermore the base paste can additionally contain the constituents (e) and/or (f), the catalyst paste additionally the constituent (e).

By the term "monofunctional" or "bi- or higher-functional ethylenically unsaturated monomers", within the meaning of the present invention, are meant polymerisable compounds which have an oligomeric or polymeric basic structure and carry at least one ethylenically unsaturated group. This ethylenically unsaturated group can be present for example as an acrylate and/or methacrylate group which is covalently bound to the basic structure. The polymeric basic structure can be e.g. a polyethylene oxide, a polyester, a polyurethane, a polycarbonate, a polyalcohol, a polystyrene or a polymerisable ethylenically unsaturated compound.

Methacrylate and acrylate monomers, such as e.g. methyl (meth)acrylate, n- or i-propyl(meth)acrylate, n-, i- or tert.butyl(meth)acrylate and 2-hydroxyl(meth)acrylate, 2-(meth)acryloxy-tetrahydrofuran, 2-(((alkylamino)-carbonyl)-oxy)ethyl-(meth)acrylates; di(meth)acrylates of propanediol, butanediol, hexanediol, octanediol, nonanediol, decanediol and eicosanediol; di(meth)acrylates of ethylene glycol, polyethylene glycols, polypropylene glycols; di(meth)acrylates of ethoxylated bisphenol A, e.g. 2,2'-bis(4-(meth)acryloxy-tetraethoxyphenyl)propane; urethane(meth)acrylates; (meth)acryl-amides are particularly preferred as monofunctional or bi- or higher-functional ethylenically unsaturated monomers of constituent (a) or (b).

Furthermore, esters of α-cyanoacrylic acid, crotonic acid, cinnamic acid, sorbic acid, vinyl ethers, such as e.g. butyl vinyl ether; mono-N-vinyl-compounds, such as N-vinyl pyrrolidone, can be used as monomers of the constituents (a) and (b).

Furthermore, the methylacrylic acid esters named in the European patent application EP-A-0 235 826, such as e.g. triglycolic acid-bis[3[4]-methacryloxymethyl-8(9)-tricyclo-[5.2.1.0$^{2.6}$]-decyl methyl ester, can be used.

Suitable in particular are 2,2-bis-4(3-methacryloxy-2-hydroxypropoxy)phenylpropane (bis-GMA), 2,2-bis-4(3-methacryloxy-propoxy)phenylpropane, triethylene glycol dimethacrylate (TEGDMA), 7,7,9-trimethyl-4,13-dioxo-3,14-dioxa-5,12-diazahexadecane-1,16-dioxy-dimethacrylate (UDMA) and di(meth)acrylates of bishydroxymethyltricyclo(5.2.1.0$^{2.6}$)-decane.

These ethylenically unsaturated monomers can be used in the disclosed dental compositions either alone or in combination with further ethylenically unsaturated monomers.

According to the invention, the bi- or higher-functional ethylenically unsaturated monomers are used in a concentration of 10 to 98.999 wt.-%, preferably from 30 to 80 wt.-%, in each case relative to the total mass of the constituents (a) to (f). A use of 45 to 70 wt.-% of constituent (a) in the polymerisable dental composition is particularly preferred.

Constituent (b) is used in a concentration of 0 to 88.999 wt.-% relative to the total mass of constituents (a) to (f). A concentration of monofunctional ethylenically unsaturated monomers according to component (b) of 0 to 58.99 wt.-%, preferably from 0 to 33.99 wt.-% is suitable in particular.

Heavy metal compounds, in particular metals of the iron or the copper groups, preferably copper are suitable as accelerator according to constituent (c). The heavy metal is suitably used in the form of soluble organic compounds. In addition, there can be added as accelerators ionogenically bound halogens or pseudohalogens, e.g. Cl-containing compounds, preferably in the form of soluble salts, in particular organic ammonium chlorides or hydrochlorides. These compounds are contained in the polymerisable dental composition in a concentration of 0 to 5 wt.-%, preferably from 0 to 3 wt.-%, particularly preferably from 0.05 to 2 wt.-%. A mixture of several accelerators can also be used.

Furthermore, the polymerisable dental composition according to the invention can contain as constituent (e) 0 to 88.999 wt.-%, in particular 10 to 68.99 wt.-% and particularly preferably 20 to 53.9 wt.-% customary fillers for dental materials, such as for example glass and quartz powders, silica gels, pyrogenic highly-dispersed silicic acids or low soluble fluorides as well as mixtures of these components. These fillers can be x-ray opaque through suitable additives, such as for example barium- or strontium-containing glasses. For example, pyrogenic highly-dispersed silicic acids are suitable as thixotropic auxiliaries. Further auxiliaries are for example dyes, pigments, flow-improvers, polymeric thickening agents or stabilizers. To increase the flexibility of the dental composition, soluble organic polymerisates such as e.g. polyvinyl acetate as well as its copolymers, can also be added.

Christobalite, calcium silicate, zirconium silicate, montmorillonites, such as bentonites, zeolites, including molecular sieves, such as sodium aluminium silicate, metallic oxide powders, such as aluminium or zinc oxides or their mixed oxides, barium sulphate, yttrium fluoride, calcium carbonate, gypsum and synthetic powders are also suitable as fillers for the dental composition according to the invention.

The named fillers can also be hydrophobized by e.g. a treatment with organosilanes or -siloxanes or by the etherification of hydroxyl groups to alkoxy groups.

The compounds described in European patent specification EP-B-0 374 824 are suitable as retarders.

The redox initiator system to be used according to the invention consists of (i) a barbituric acid derivative and/or a malonyl sulfamide and (ii) an organic peroxide, selected from the group of the mono- or multifunctional carboxylic acid peroxide esters. There can be used as barbituric acid derivatives, for example, 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 1-benzyl-5-phenylbarbituric acid, 1-cyclohexyl-5-ethylbarbituric acid and the thiobarbituric acids mentioned in the German patent application DE-A-42 19 700.

The barbituric acids and barbituric acid derivatives described in German patent specification DE-C-14 95 520 as well as the malonyl sulfamides named in the European patent specification EP-B-0 059 451 are well suited. Preferred malonyl sulfamides are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide or 2,6-dioctyl-4-isobutylmalonyl sulfamide.

The redox initiator system according to the invention contains mono- or multifunctional carboxylic acid peroxyesters as organic peroxides. Carbonic peroxyesters are also included among the multifunctional carboxylic acid peroxyesters within the meaning of the present application.

Suitable are for example carbonic-diisopropyl-peroxydiester, neodecanoic acid-tertiarybutyl-peroxyester, neodecanoic acid-tertiaryamyl-peroxyester, maleic acid-tertiarybutyl-monoperoxyester, benzoic acid-tertiarybutyl-peroxyester, 2-ethylhexanoic acid-tertiarybutyl-peroxyester, 2-ethylhexanoic acid-tertiaryamyl-peroxyester, carbonic-monoisopropylester-monotertiarybutyl-peroxyester, carbonic-dicyclohexyl-peroxyester, carbonic-dimyristyl-peroxyester, carbonic dicetyl-peroxyester, carbonic-di(2-ethylhexyl)-peroxyester, carbonic-tertiarybutyl-peroxy-(2-ethylhexyl)ester or 3,5,5-trimethylhexanoic acid-tertiarybutyl-peroxyester, benzoic acid-tertiaryamyl-peroxyester, acetic acid-tertiarybutyl-peroxyester, carbonic-di(4-tertiarybutyl-cyclohexyl)-peroxyester, neodecanoic acid-cumene-peroxyester, pivalic acid-tertiaryamyl-peroxyester and pivalic acid tertiarybutyl-peroxyester.

In particular, carbonic-tertiarybutyl-peroxy-(2-ethylhexyl)ester or 3,5,5-trimethyl-hexanoic acid-tertiarybutyl-peroxyester can be used as organic peroxides according to the invention.

The dental compositions according to the invention contain the redox initiator system in a concentration of 0.001 to 5 wt.-%, preferably in a concentration of 0.01 to 3 wt.-%, relative to the total mass of the constituents (a) to (f). An initiator system concentration of 0.05 to 2 wt.-% is particularly preferred.

As constituent (f) the polymerisable dental composition according to the invention contains 1 to 30 wt.-%, preferably 1 to 20 wt.-%, in particular 1 to 15 wt.-%, of a customary plasticizer or a mixture of customary plasticizers. These are for example polyethylene glycol derivatives, polypropylene glycols, low-molecular-weight polyesters, dibutyl-, dioctyl-, dinonyl-, diphenylphthalate, di(iso-nonyladipate), tricresylphosphate and silicone oils.

For the following examples the dental compositions according to the invention were prepared as two-component paste systems in the form of base and catalyst pastes. The base paste contained the constituents (a), (b), (c) and (e) in the amounts in wt.-% that can be seen from Table 1. Constituent (f) can alternatively also be added. The catalyst paste contained the constituents (d), (e) and (f), the inclusion of (e) not being obligatory. To prepare the two pastes, the respective constituents of the base and catalyst pastes were kneaded to homogenous pastes with a 3-arm kneader under vacuum.

The catalyst pastes 1, 2 and 3 contained customary peroxides known from the state of the art. These pastes served to prepare comparative tests. The catalyst pastes 4 and 5 included the peroxides according to the invention.

For the following tests a mixture ratio of base-to-catalyst paste of 10:1 was selected. Naturally, the two-component systems according to the invention can also be prepared with other mixture ratios.

TABLE 1

| | | |
|---|---|---|
| BASE PASTE | glass powder | 34 wt.-% |
| | microfine silicic acid | 8 wt.-% |
| | bis-(1-phenylpentane-1,3-dionato)-copper(II) | 0.0013 wt.-% |
| | (β-phenylethyl)-dibutyl-ammonium-chloride | 0.36 wt.-% |
| | 2,2-bis-{4-[oligo(ethoxy))phenyl}-propane-dimethacrylate | made up 100 wt.-% |
| CATALYST PASTE 1 | glass powder | 34 wt.-% |
| | microfine silicic acid | 8 wt.-% |
| | 1-benzyl-5-phenylbarbituric acid | 0.6 wt.-% |
| | 2,2-bis-4-(2-hydroxyethoxy-phenyl)-propane-bis-acetate | made up 100 wt.-% |
| | dibenzoyl peroxide | 3.9 wt.-% |
| CATALYST PASTE 2 | glass powder | 34 wt.-% |
| | microfine silicic acid | 8 wt.-% |
| | 1-benzyl-5-phenylbarbituric acid | 0.6 wt.-% |
| | 2,2-bis-4-(2-hydroxyethoxy-phenyl)-propane-bis-acetate | made up 100 wt.-% |
| | dilauroyl peroxide | 8.0 wt.-% |
| CATALYST PASTE 3 | glass powder | 34 wt.-% |
| | microfine silicic acid | 8 wt.-% |
| | 1-benzyl-5-phenylbarbituric acid | 0.3 wt.-% |
| | 2,2-bis-4-(2-hydroxyethoxy-phenyl)-propane-bis-acetate | made up 100 wt.-% |
| | cumene hydroperoxide | 0.48 wt.-% |
| CATALYST PASTE 4 | glass powder | 34 wt.-% |
| | microfine silicic acid | 8 wt.-% |
| | 1-benzyl-5-phenylbarbituric acid | 0.6 wt.-% |
| | 2,2-bis-4-(2-hydroxyethoxy-phenyl)-propane-bis-acetate | made up 100 wt.-% |
| | carbonic-tertiarybutylperoxy-(2-ethylhexyl)ester | 0.6 wt.-% |
| CATALYST PASTE 5 | glass powder | 34 wt.-% |
| | microfine silicic acid | 8 wt.-% |
| | 1-benzyl-5-phenylbarbituric acid | 0.6 wt.-% |
| | 2,2-bis-4-(2-hydroxyethoxy phenyl)-propane-bis-acetate | made up 100 wt.-% |
| | 3,5,5-trimethylhexanoic acid-tertiarybutylperoxyester | 0.6 wt.-% |

The various catalyst pastes of the dental compositions according to the invention were stored for extended periods and the setting times of the dental compositions mixed from the two components were measured at various storage times.

The setting times were measured after a maximum of 3 days' storage at room temperature. This value is shown in Table 2 as starting value. The catalyst paste was then stored in a heating cabinet at 50° C. and the setting time checked after the stated time intervals (see Table 2). The base paste was stored at room temperature. The hot storage at 50° C. is a generally recognised test under stress conditions which, on the basis of the results which are obtained at increased temperatures, permits conclusions to be drawn about the stability during storage under normal temperatures. These temperatures are however also completely realistic, as the dental compositions described can be subjected to such temperatures during transportation.

The setting times were measured as follows:

The base paste (1.00 g) and the corresponding catalyst pastes 1–5 (0.10 g) were weighed in on a mixing block and homogenously mixed. The setting time of the mixed paste was measured using a curometer (Wallace-Shawbury, England).

The results of the setting times measured are shown in Table 2, the expression >20 mins meaning that complete setting was not observed within 20 mins and therefore the test in question was terminated.

TABLE 2

|  | Start | 1 day (50° C.) | 3 days (50° C.) | 1 week (50° C.) | 2 weeks (50° C.) | 3 weeks (50° C.) |
|---|---|---|---|---|---|---|
| CATALYST PASTE 1 |  |  |  |  |  |  |
| setting time [min'sec] | 2'55 | >20'00 | >20'00 | >20'00 | >20'00 | >20'00 |
| CATALYST PASTE 2 |  |  |  |  |  |  |
| setting time [min'sec] | 2'35 |  | >20'00 | >20'00 | >20'00 | >20'00 |
| CATALYST PASTE 3 |  |  |  |  |  |  |
| setting time [min'sec] | 3'45 |  | >20'00 | >20'00 | >20'00 | >20'00 |
| CATALYST PASTE 4 |  |  |  |  |  |  |
| setting time [min'sec] | 2'00 | 2'00 | 2'05 | 2'25 | 2'25 | 2'35 |
| CATALYST PASTE 5 |  |  |  |  |  |  |
| setting time [min'sec] | 2'05 | 2'00 | 1'55 | 1'55 | 2'00 | 2'10 |

What is claimed is:

1. A polymerizable dental composition comprising:
   (a) 10 to 98.999 wt. % of at least one bi- or higher-functional ethylenically unsaturated monomer,
   (b) 0 to 88.999 wt. % of at least one monofunctional ethylenically unsaturated monomer,
   (c) 0.05 to 5 wt. % of an accelerator,
   (d) 0.001 to 5 wt. % of a redox initiator system which can initiate radical polymerisation, and
   (e) 0 to 88.999 wt. % of at least one of one or more fillers, thixotropic auxiliaries, retarders and other auxiliaries,
   (f) 1 to 30 wt. % of a plasticizer,
   wherein the redox initiator system comprises (i) barbituric acid or a substituted barbituric acid and/or a malonyl sulfamide and (ii) an organic peroxide that is a mono- or multifunctional carboxylic acid peroxyester,
   wherein the constituents (a), (b) and (c) constitute a base paste, the constituent (d) constitutes a catalyst paste spatially separated from the base paste, the constituent (e) is optionally present in either or both of the base paste and the catalyst paste and the constituent (f) is present in one or the other or both of the catalyst paste and the base paste.

2. The polymerizable dental composition of claim 1, in which the carboxylic acid peroxyester is a carboxylic acid alkyl peroxyester.

3. The polymerizable dental composition according to claim 2, in which the alkyl group of the organic peroxide is branched or cyclic.

4. The polymerizable dental composition according to claim 2, in which the alkyl group of the organic peroxide is linear.

5. The polymerizable dental composition according to claim 2, in which the carboxylic acid alkyl peroxyester is selected from the group consisting of carbonic-diisopropyl-peroxydiester, neodecanoic acid tertiarybutyl-peroxyester, neodecanoic acid-tertiaryamyl-peroxyester, maleic acid-tertiarybutyl-monoperoxyester, benzoic acid-tertiarybutyl-peroxyester, 2-ethylhexanoic acid-tertiarybutyl-peroxyester, 2-ethylhexanoic acid-tertiaryamyl-peroxyester, carbonic-monoisopropylester-monotertiarybutyl-peroxyester, carbonic-dicyclohexyl-peroxyester, carbonic-dimyristyl-peroxyester, carbonic dicetyl-peroxyester, carbonic-di(2-ethylhexyl)-peroxyester, carbonic-tertiarybutyl-peroxy-(2-ethylhexyl)ester, 3,5,5-trimethylhexanoic acid-tertiarybutyl-peroxyester, benzoic acid-tertiaryamyl-peroxyester, acetic acid-tertiarybutyl-peroxyester, carbonic-di(4-tertiarybutyl-cyclohexyl)-peroxyester, neodecanoic acid-cumene-peroxyester, pivalic acid-tertiaryamyl-peroxyester and pivalic acid tertiarybutyl-peroxyester.

6. The polymerizable dental composition according to claim 1, in which the organic peroxide is carbonic-tertiarybutyl-peroxy-(2-ethylhexyl)ester or 3,5,5-trimethylhexanoic acid-tertiarybutyl-peroxyester.

7. The polymerizable dental composition according to claim 1, in which constituent (a) is present in a concentration of 30 to 80 wt. %.

8. The polymerisable dental composition according to claim 1, in which constituent (a) is present in a concentration of 45 to 70 wt. %.

9. The polymerisable dental composition according to claim 1, in which constituent (b) is present in a concentration of 0 to 58.99 wt. %.

10. The polymerisable dental composition according to claim 1, in which constituent (b) is present in a concentration of 0 to 33.9 wt. %.

11. The polymerisable dental composition according to claim 8, in which constituent (b) is present in a concentration of 0 to 58.99 wt. %.

12. The polymerisable dental composition according to claim 9, in which constituent (b) is present in a concentration of 0 to 33.9 wt. %.

13. The polymerizable dental composition according to claim 1, in which constituent (c) is present in a concentration of 0.05 to 3 wt. %.

14. The polymerizable dental composition according to claim 1, in which constituent (c) is present in a concentration of 0.05 to 2 wt. %.

15. The polymerizable dental composition according to claim 8, in which constituent (c) is present in a concentration of 0.5 to 3 wt. %.

16. The polymerizable dental composition according to claim 9, in which constituent (c) is present in a concentration of 0.05 to 2 wt. %.

17. The polymerizable dental composition according to claim 10, in which constituent (c) is present in a concentration of 0.05 to 3 wt. %.

18. The polymerizable dental composition according to claim 11, in which constituent (c) is present in a concentration of 0.05 to 2 wt. %.

19. The polymerizable dental composition according to claim 12, in which constituent (c) is present in a concentration of 0.05 to 3 wt. %.

20. The polymerizable dental composition according to claim 1, in which constituent (d) is present in a concentration of 0.01 to 3 wt. %.

21. The polymerizable dental composition according to claim 1, in which constituent (d) is present in a concentration of 0.05 to 2 wt. %.

22. The polymerizable dental composition according to claim 8, in which constituent (d) is present in a concentration of 0.01 to 3 wt. %.

23. The polymerizable dental composition according to claim 9, in which constituent (d) is present in a concentration of 0.05 to 2 wt. %.

24. The polymerizable dental composition according to claim 10, in which constituent (d) is present in a concentration of 0.01 to 3 wt. %.

25. The polymerizable dental composition according to claim 11, in which constituent (d) is present in a concentration of 0.05 to 2 wt. %.

26. The polymerizable dental composition according to claim 12, in which constituent (d) is present in a concentration of 0.01 to 3 wt. %.

27. The polymerizable dental composition according to claim 13, in which constituent (d) is present in a concentration of 0.05 to 2 wt. %.

28. The polymerizable dental composition according to claim 14, in which constituent (d) is present in a concentration of 0.01 to 3 wt. %.

29. The polymerizable dental composition according to claim 15, in which constituent (d) is present in a concentration of 0.05 to 2 wt. %.

30. The polymerizable dental composition according to claim 16, in which constituent (d) is present in a concentration of 0.01 to 3 wt. %.

31. The polymerizable dental composition according to claim 17, in which constituent (d) is present in a concentration of 0.05 to 2 wt. %.

32. The polymerizable dental composition according to claim 18, in which constituent (d) is present in a concentration of 0.01 to 3 wt. %.

33. The polymerizable dental composition according to claim 19, in which constituent (d) is present in a concentration of 0.05 to 2 wt. %.

34. The polymerizable dental composition according to claim 1, in which constituent (e) is present in a concentration of 10 to 68.99 wt. %.

35. The polymerizable dental composition according to claim 1, in which constituent (e) is present in a concentration of 20 to 53.9 wt. %.

36. The polymerisable dental composition according to claim 1, in which constituent (f) is present in a concentration of 1 to 20 wt. %.

37. The polymerisable dental composition according to claim 1, in which constituent (f) is present in a concentration of 1 to 15 wt. %.

38. A polymerizable dental composition comprising:
 (a) 10 to 98.999 wt. % of at least one bi- or higher-functional ethylenically unsaturated monomer,
 (b) 0 to 88.999 wt. % of at least one monofunctional ethylenically unsaturated monomer, and
 (c) 0.001 to 5 wt. % of a redox initiator system which can initiate radical polymerisation,
 wherein the redox initiator system comprises (i) barbituric acid or a substituted barbituric acid and/or a malonyl sulfamide and (ii) an organic peroxide that is a mono- or multifunctional carboxylic acid alkyl peroxyester,
 wherein the constituents (a) and (b) are separately present from constituent (c) among at least two pastes spatially separated from each other;
 and a plasticizer in an amount of from 1 to 30 wt. % that is present in one or the other or both of the paste containing (c) and the paste containing (a) and (b).

39. The polymerizable dental composition according to claim 38, in which the alkyl group of the organic peroxide is branched or cyclic.

40. The polymerizable dental composition according to claim 38, in which the alkyl group of the organic peroxide is linear.

41. The polymerizable dental composition according to claim 38, in which the carboxylic acid alkyl peroxyester is selected from the group consisting of carbonic-diisopropyl-peroxydiester, neodecanoic acid tertiarybutyl-peroxyester, neodecanoic acid-tertiaryamyl-peroxyester, maleic acid-tertiarybutyl-monoperoxyester, benzoic acid-tertiarybutyl-peroxyester, 2-ethylhexanoic acid-tertiarybutyl-peroxyester, 2-ethylhexanoic acid-tertiaryamyl-peroxyester, carbonic-monoisopropylester-monotertiarybutyl-peroxyester, carbonic-dicyclohexyl-peroxyester, carbonic-dimyristyl-peroxyester, carbonic dicetyl-peroxyester, carbonic-di(2-ethylhexyl)-peroxyester, carbonic-tertiarybutyl-peroxy-(2-ethylhexyl)ester, 3,5,5-trimethylhexanoic acid-tertiarybutyl-peroxyester, benzoic acid-tertiaryamyl-peroxyester, acetic acid-tertiarybutyl-peroxyester, carbonic-di(4-tertiarybutyl-cyclohexyl)-peroxyester, neodecanoic acid-cumene-peroxyester, pivalic acid-tertiaryamyl-peroxyester and pivalic acid tertiarybutyl-peroxyester.

42. The polymerizable dental composition according to claim 38, in which the organic peroxide is carbonic-tertiarybutyl-peroxy-(2-ethylhexyl)ester or 3,5,5-trimethylhexanoic acid-tertiarybutyl-peroxyester.

43. A method for preparing a dental filling material, a stump build-up material, a fixing cement, a temporary crown or bridge material, or a dental material for the preparation of inlays, onlays, facing shells, or modelling materials, comprising polymerizing the composition of claim 1.

* * * * *

UNITED STATES PATENT AND TRADEMARK OFFICE
CERTIFICATE OF CORRECTION

| | |
|---|---|
| PATENT NO. | : 6,852,775 B1 |
| APPLICATION NO. | : 10/018660 |
| DATED | : February 8, 2005 |
| INVENTOR(S) | : Wolfgang Soglowek |

It is certified that error appears in the above-identified patent and that said Letters Patent is hereby corrected as shown below:

Column 1
Lines 41-47, delete "acceptable in the dental ---------------- pulpa." and insert the following paragraphs:

-- When using these materials the monomers are mixed with suitable initiator systems shortly before being processed, a pasty composition forming which cures by radical polymerisation. The original components, which contain monomer and initiator systems among others, can also be present in the form of pastes spatially separated from each other or also as a powder-liquid system.

Various initiator systems are used to start the radical polymerisation. It is necessary that, after the polymerisation has started, the processing time until the material is cured is long enough to give the dentist enough time for the material to be matched and made available for processing. At the same time, however, the setting time from the beginning of gelling to an extensive curing of the material is also to be as short as possible, as working is not possible during this phase and the waiting time for the dentist and the patient should be as short as possible.

An initiator system already known for a long time consists of an amine and a peroxide component, such as described e.g. in patent specification DE-C-975 072. The polymerisation is started in this case by the peroxide compound. A tertiary amine is used for example to accelerate the polymerisation. Another such system is also described by Albert GroB in "Quintessenz der Zahntechnik", 1977, 7, Paper No. 293. There, secondary or tertiary amines accelerate the decomposition of the peroxide component, which triggers the polymerisation of the material. The amine component is normally introduced into a paste, the so-called base paste. This base paste also contains the monomers provided for polymerisation. The peroxide component is introduced into a further paste, the so-called catalyst paste. The spatial separation of the two initiator components is necessary in order to avoid a premature curing of the monomer portions. Also described in the German patent specification DE-C-955 633 is a similar initiator system for the polymerisation of unsaturated hydrocarbons which contains heavy metals as well as an amine and a sulphone component. An initiator system with an organic peroxide compound and a tertiary aromatic amine as activator (accelerator) is also named in the European patent specification EP-13-374 824.

A disadvantage of the materials named is that the amines suitable for a favourable setting phase tend to discolour. These yellow-brown discolorations are however not acceptable in the dental field. In addition, tertiary aromatic amines can be used only under certain conditions due to their health risk. Furthermore, the increase in temperature during polymerisation of these systems, due to the exothermic reaction processes, causes problems. Too great a development of heat can lead to damage to the patient's pulpa. --

UNITED STATES PATENT AND TRADEMARK OFFICE
CERTIFICATE OF CORRECTION

PATENT NO. : 6,852,775 B1
APPLICATION NO. : 10/018660
DATED : February 8, 2005
INVENTOR(S) : Wolfgang Soglowek It is certified that error appears in the above-identified patent and that said Letters Patent is hereby corrected as shown below:

<u>Column 4</u>
Line 2, after "14" insert -- , --.

<u>Column 8</u>
Line 46, in Claim 15, delete "0.5" and insert -- 0.05 --, therefor.

Signed and Sealed this

Twenty-seventh Day of May, 2008

JON W. DUDAS
*Director of the United States Patent and Trademark Office*